United States Patent [19]
Trovato

[11] Patent Number: 5,641,285
[45] Date of Patent: Jun. 24, 1997

[54] MAXILLARY MODEL POSITIONING METHOD AND APPARATUS

[76] Inventor: Joseph P. Trovato, 445 Belgrove Dr., Kearny, N.J. 07032

[21] Appl. No.: 420,407

[22] Filed: Apr. 12, 1995

[51] Int. Cl.⁶ .................................................. A61C 11/00
[52] U.S. Cl. .................. 433/56; 433/60; 433/72
[58] Field of Search ...................... 433/54, 56, 59, 433/60, 68, 72, 57

[56]  References Cited

U.S. PATENT DOCUMENTS

| | | |
|---|---|---|
| 3,465,443 | 9/1969 | Schwartz et al. . |
| 4,155,163 | 5/1979 | Schwartz ................................. 433/56 |
| 4,278,426 | 7/1981 | Schwartz . |
| 4,500,289 | 2/1985 | Garganese et al. ....................... 433/54 |
| 4,528,627 | 7/1985 | Cohen . |
| 4,609,351 | 9/1986 | Blair ................................... 433/56 X |
| 4,611,991 | 9/1986 | Heinix ................................ 433/54 X |
| 4,668,189 | 5/1987 | Levandoski . |
| 5,278,756 | 1/1994 | Lemchen et al. . |
| 5,318,441 | 6/1994 | Keller . |
| 5,320,527 | 6/1994 | Schwartz ................................. 433/49 |

OTHER PUBLICATIONS

Schwartz, Robert, D.D.S., "Standardization of Diagnostic Casts: Description of Technique," New York Journal of Dentistry, vol. 37, No. 9, pp. 327–336, Nov. 1967.

*Primary Examiner*—Nicholas D. Lucchesi
*Attorney, Agent, or Firm*—Charles E. Brazga

[57]  ABSTRACT

Disclosed are a method and apparatus for relating a model of a maxillary arch of a patient to a simulated axis of rotation of the condyle of the lower jaw of the patient. In carrying out the invention in one form, a pointer is positioned on a predetermined landmark of the upper jaw of a patient. A lateral image of the condyle and the pointer are obtained while the patient's two hamular notches and incisive papilla define a plane which, preferably, is substantially horizontal. From the image, vertical and front-to-back distances of the axis of rotation of the condyle relative to the landmark are then determined. A model of a maxillary arch of a patient is positioned such that the predetermined landmark is located with substantially the same vertical and front-to-back distances from a simulated axis of rotation of the patient's lower jaw. Finally, a model of the patient's lower jaw that rotates about the simulated axis is positioned to abut the model of the maxillary arch.

15 Claims, 4 Drawing Sheets

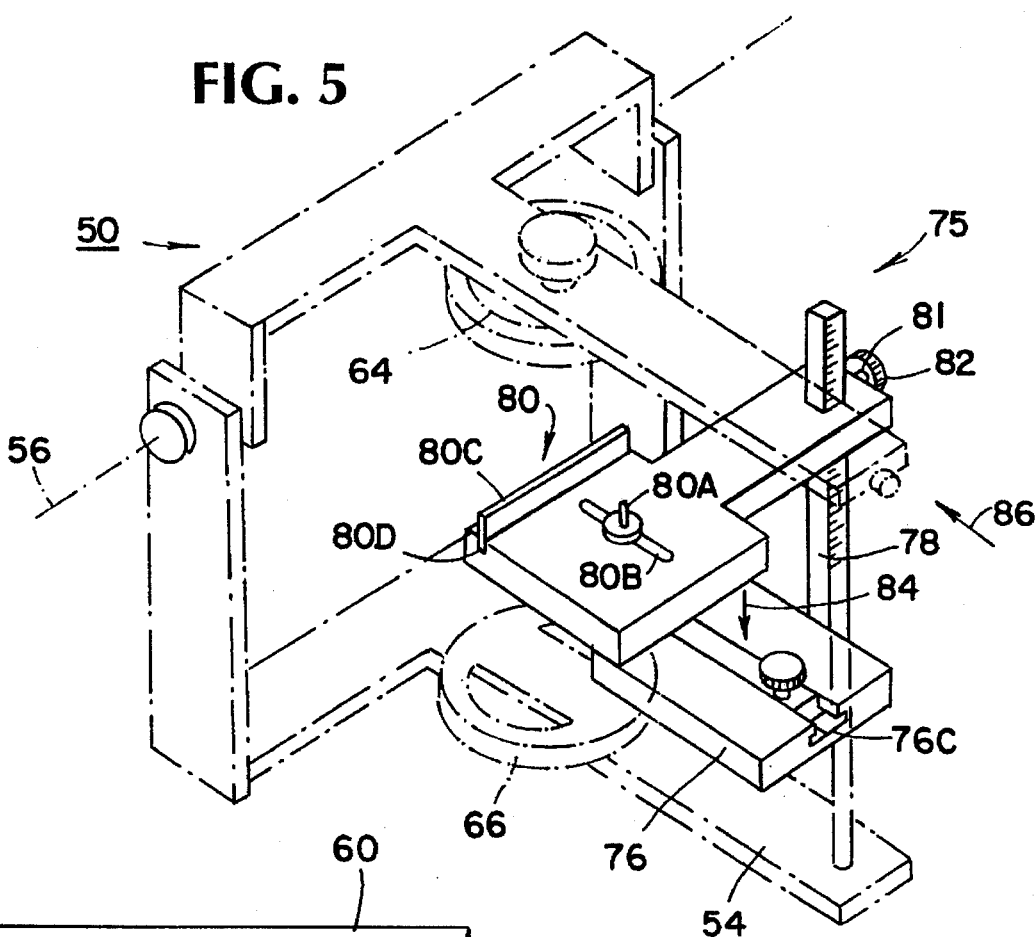
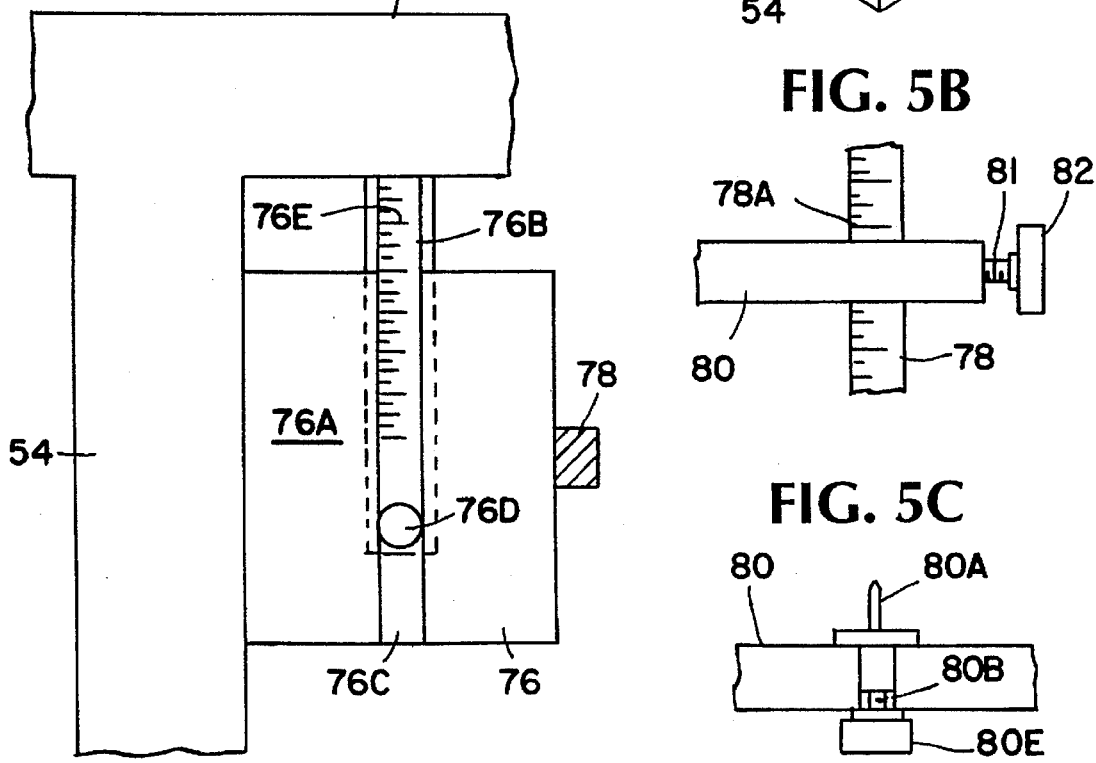

MAXILLARY MODEL POSITIONING METHOD AND APPARATUS

FIELD OF THE INVENTION

The present invention relates to method and apparatus for accurately positioning, or "relating," a model of a maxillary arch of a patient to a simulated axis of rotation of the condyle of the lower jaw of the patient. In this way, a model of a corresponding, mandibular arch of the patient can then be accurately positioned by placing it beneath the model of the maxillary arch. This allows a dentist to accurately evaluate or produce dental appliances without the patient being present. It also allows the dentist to give the positional coordinates to a third party (e.g., dental laboratory) for the same purpose.

BACKGROUND OF THE INVENTION

In the field of dentistry, it is standard practice to create a cast, or model, of the maxillary arch of a patient, and a corresponding cast, or model, of the corresponding mandibular arch of the patient. It is standard to relate the models to each other with respect to a simulated axis of rotation of the condyle of the patient's lower jaw; "relate" meaning to position with respect to each other. Both models are typically held by a device known in the art as an articulator. An articulator has an upper arm hinged to a lower arm about a main axis of the articulator. The maxillary model is attached to the upper arm, and the mandibular model is attached to the lower arm. The axis of the articulator constitutes the mentioned simulated axis of rotation of the condyle of the patient's lower jaw.

Standard practice has been to use a so-called face bow for positioning the maxillary model with respect to the simulated axis of rotation. Such a device is shown, for instance, in U.S. Pat. No. 4,668,189. In FIG. 1 of such patent, the face bow is shown in phantom as it is used in connection with an articulator. The present invention is particularly directed to replacing the use of a face bow entirely in the foregoing operation.

Briefly, in using a prior art face bow, a patient first bites his or her upper teeth into a bite fork of the face bow. A first type of face bow has a pair of aligned, spaced pointers that are inserted into the ear canals of the patient while the patient is biting on the bite fork of the device. The bite fork and pointers are then fixed in position with respect to each other. The face bow is removed from the patient, and then used in conjunction with an articulator for positioning a maxillary model with respect to the main axis of rotation of the articulator. The pointers of the face bow are positioned at a standard deviation of approximately 13 millimeters from the main axis of the articulator. Such standard deviation is an approximation of the actual deviation from the ear canal of a patient to his or her axis of rotation of the condyle of the patient's lower jaw.

A drawback to using the foregoing type of face bow is that the standard deviation mentioned above differs in many cases from the actual deviation from the ear canal of a patient to his or her axis of rotation of the condyle of the patient's lower jaw. This can result in inaccuracies in the relationship of the maxilla (i.e., upper jaw) to the hinge axis, which in turn may lead to discrepancies in anything produced with the articulator.

The foregoing problem is avoided by another type of face bow, known as a non-arbitrary face bow. This is because such type of face bow has pointers placed on the condyles whose location is determined by palpation. However, both the non-arbitrary type of face bow, and the first-mentioned face bow suffer from the drawback, during positioning of a face bow onto a patient's features (as described above), when the patient's upper teeth are separated form his or her lower teeth by the inherent vertical spacing of the bite fork of the face bow. Such vertical spacing typically gives rise to an inaccuracy in positioning a maxillary model with respect to the axis of the condyle of a patient's lower jaw. This is because such axis normally shifts position as a patients upper and lower teeth are spaced vertically apart. For instance, if a typical adult separates his or her upper and lower teeth, the axis of the condyle of his or her lower jaw can move down and forward, relative to a closed-bite position, by at least several millimeters.

The foregoing drawback further results in dental appliances produced from the so-positioned maxillary and mandibular models not being predictably formed in an accurate manner.

SUMMARY OF THE INVENTION

A primary object of the invention is to provide a method and apparatus for accurately relating a model of a maxillary arch of a patient to a simulated axis of rotation of the condyle of the lower jaw of the patient.

The foregoing object is achieved by the invention, comprising a method and apparatus for relating a model of a maxillary arch of a patient to a simulated axis of rotation of the condyle of the lower jaw of the patient. In carrying out the invention in one form, a pointer is positioned on a predetermined landmark of the upper jaw of a patient. A lateral image of the condyle and the pointer are obtained while the patient's two hamular notches and incisive papilla define a plane that, preferably, is substantially horizontal. From the image, vertical and front-to-back distances of the axis of rotation of the condyle relative to the landmark are then determined. A model of a maxillary arch of a patient is positioned such that the predetermined landmark is located with substantially the same vertical and front-to-back distances from a simulated axis of rotation of the patient's lower jaw. Finally, a model of the patient's lower jaw that rotates about the simulated axis is positioned to abut the model of the maxillary arch.

BRIEF DESCRIPTION OF THE DRAWING FIGURES

The foregoing, and further, objects and advantages of the invention will become apparent from the following description when read in conjunction with the drawing, in which:

FIG. 5 is a perspective view of a novel dental cast relator, also showing the articulator of FIG. 4 in phantom.

Figure 1:
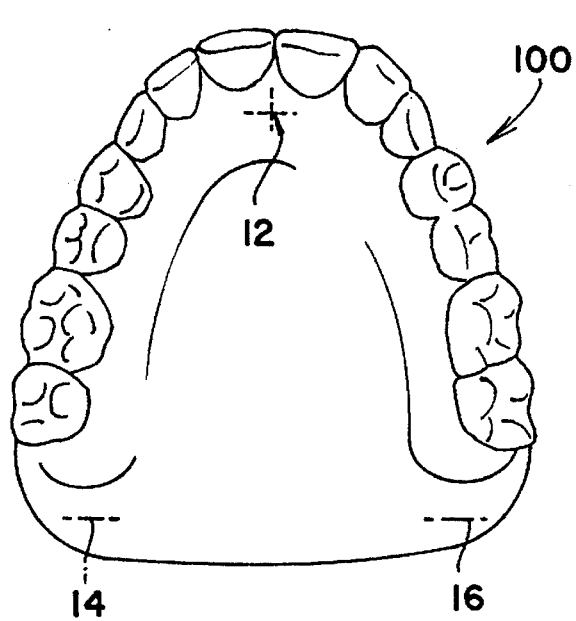
FIG. 1 is a view of an occlusal surface of a maxillary arch of a patient.

FIG. 5A is a detail, plan view of base member 76 of relator 75 of FIG. 5, taken at arrow 84 in FIG. 5, together with lower arm 54 and lower beam 60 of an articulator.

FIG. 5B is a detail view, taken at arrow 86 in FIG. 5 and showing upright beam 78 and table 80 of that figure.

FIG. 5C is a detail view of incisal pin 80A and surrounding structure of FIG. 5.

Figure 6:
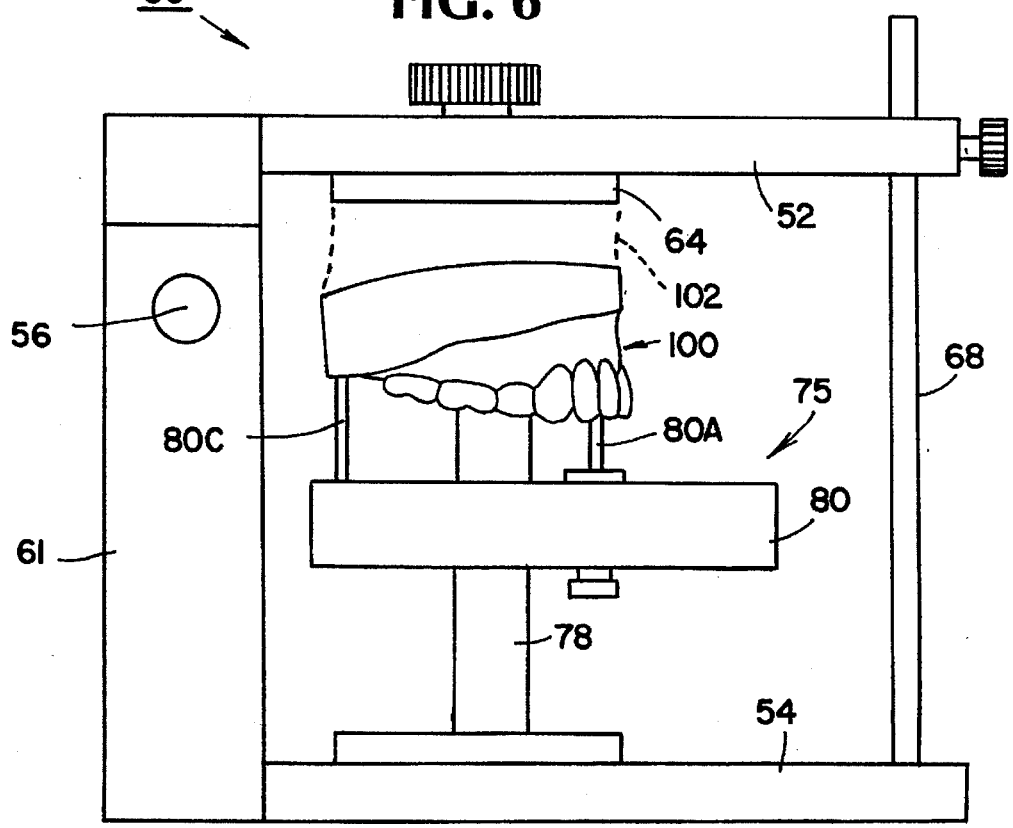

FIG. 6 is a side plan view illustrating the positioning of a model of a maxillary arch of a patient with respect to a simulated axis of rotation of the condyle of a patient's mandibular, or lower, jaw.

Figure 7:
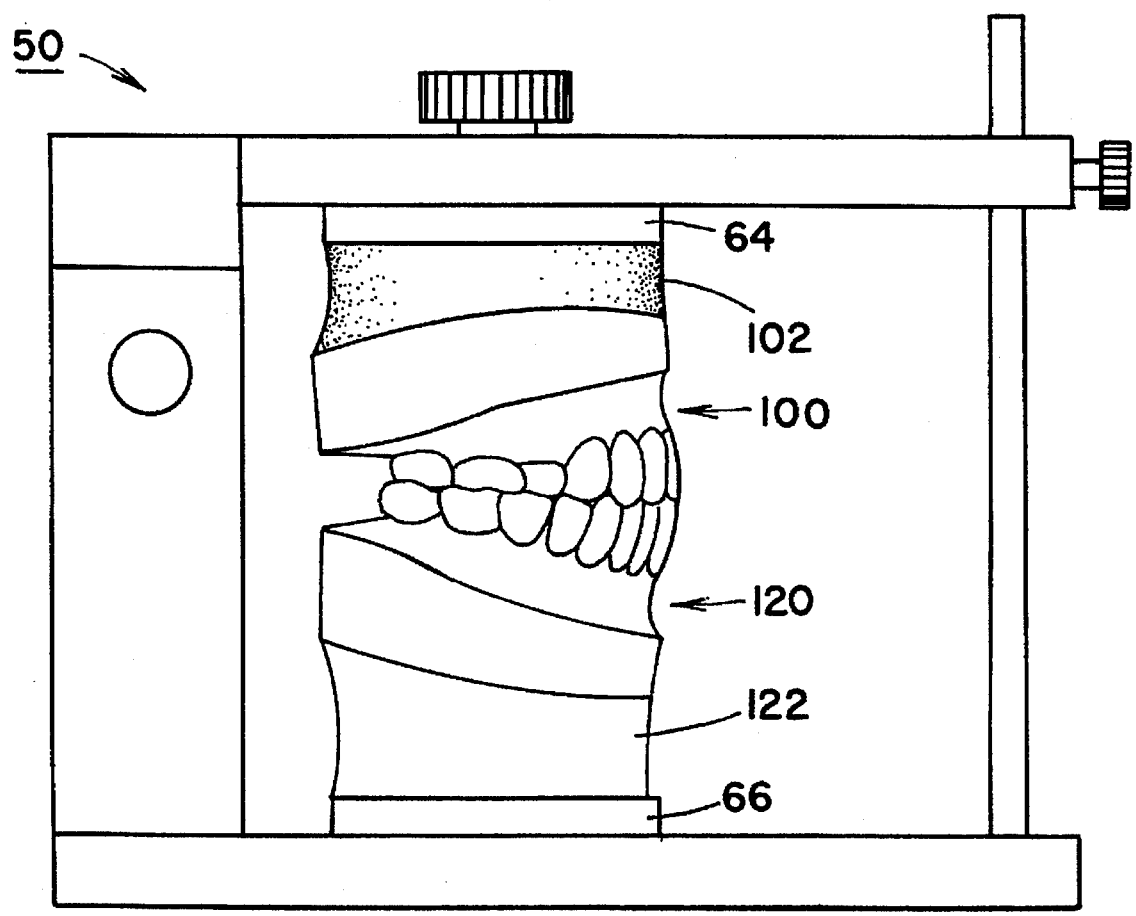

FIG. 7 is similar to FIG. 6, additionally showing the inclusion of a model of a mandibular arch of a patient.

DETAILED DESCRIPTION OF THE PREFERRED EMBODIMENTS

FIG. 1 shows an occlusal view of a maxillary arch 100 of a patient. Three landmarks are shown in phantom: an incisive papilla 12, located behind the front teeth; and a pair of hamular notches 14 and 16, respectively located to the rear of the patient's molars. The foregoing landmarks are, of course, also contained in the patient's maxillary arch. These landmarks are substantially constant throughout a patient's adult life and are not distorted by the relatively changeable position of the patient's teeth. These three landmarks, moreover, can be used as described below to define a plane that is substantially horizontal.

Figure 2:
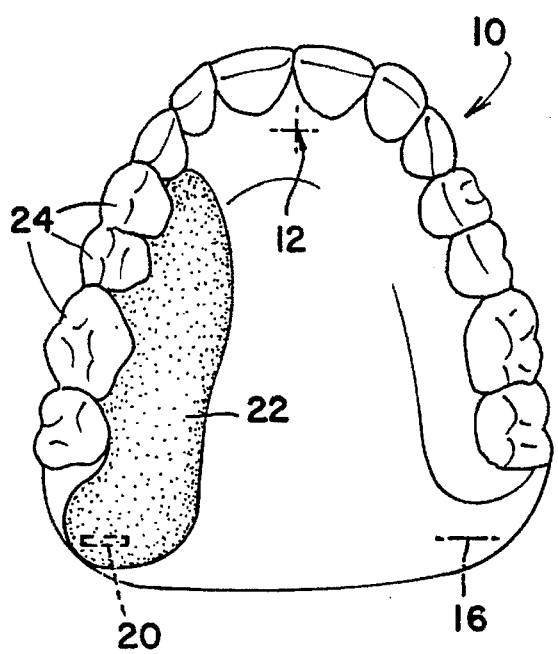
FIG. 2 is similar to FIG. 1, additionally showing the placement of a pointer at the location of a landmark of the maxillary arch of a patient.

In accordance with the present invention, a marker or pointer is positioned at one of the foregoing landmarks, or, alternatively, at another landmark such as the back of a patient's tooth. FIG. 2 shows an exemplary pointer or marker 20 positioned so as to overlie hamular notch 14 (shown in FIG. 1). Pointer 20 may conveniently be held in place with a dental acrylic 22 that is easily formed next to molars 24 and adjacent surfaces of the maxillary arch. Acrylic 22 may, for instance, comprise Triad-brand acrylic sold by Dentsply/York Division of York, Pa. It can be rapidly hardened by exposure to light. Pointer 20 may conveniently comprise 16-gauge stainless steel wire, for instance, where radiographic imaging means (not shown) are used to obtain an image of the condyle of the patient's lower jaw and of the pointer.

In order for the patient's incisive papilla 12 and hamular notches 14 and 16 (FIG. 1) to define a substantially horizontal plane, it is standard practice to obtain a lateral radiographic image of the patient's skull when the patient is looking straight ahead at a target on a wall placed at the patient's eye level. The radiograph is taken from a standard distance, e.g., 60 inches, resulting in an ascertainable magnification factor.

Figure 3:
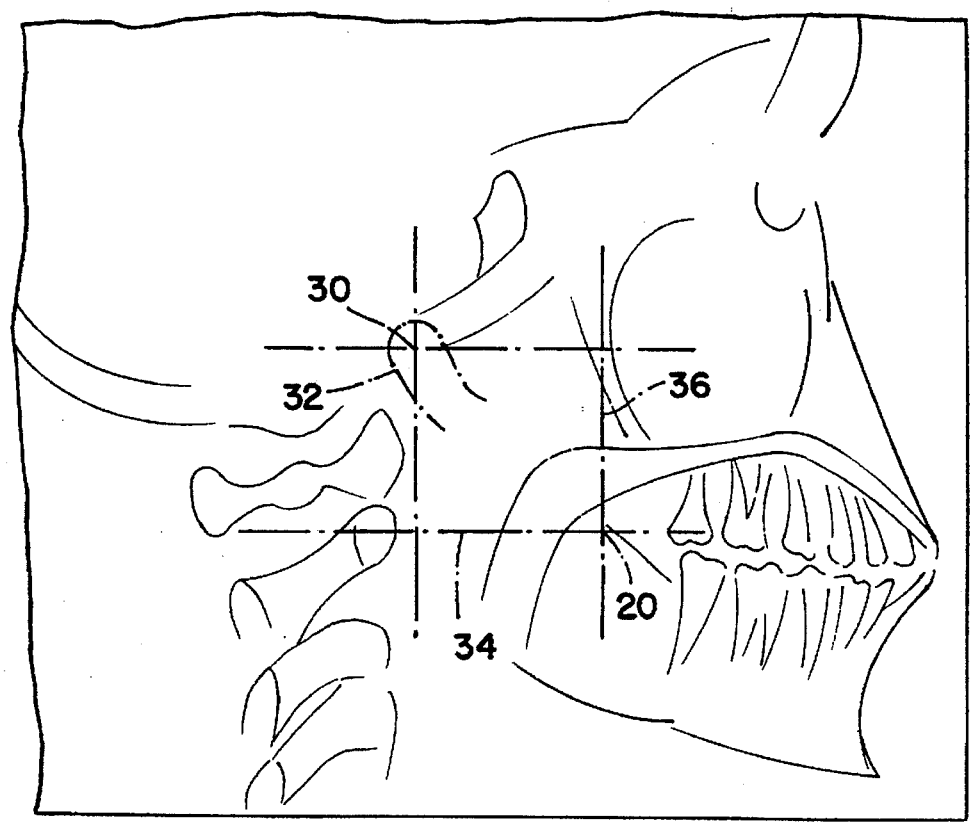
FIG. 3 is a radiographic lateral skull image of a patient, showing the condyle of the patient's lower jaw as well as a pointer that has been prepositioned at a landmark on the patient's maxillary arch.

A radiographic image so obtained of a patient is shown in FIG. 3. Pointer 20 appears as a point in the radiograph. A further point 30, representing the axis of rotation of the condyle of the patient's lower jaw, is shown within an outline 32 of such condyle. Tracing the condyle to create such outline is useful in locating point 30, which is approximately at the circular center of the upper end of the condyle. Taking into account the magnification factor of the radiographic (or other) image used, the forward-backward distance 34 between condyle axis point 30 and pointer 20 can be easily determined. The same is true for the vertical distance 36 between condyle point 30 and pointer 20. By "forward-backward distance" is meant the dimension forward or backward from the patient whose lateral skull image is shown.

Forward-backward distance 34 and vertical distance 36 are then used to relate a model of the maxillary arch of the patient to a simulated axis of rotation of the condyle of the lower jaw of the patient. This can be accomplished using several devices, one of which is known in the art and referred to as an articulator. A prior art articulator 50 is shown in simplified form in FIG. 4.

Figure 4:
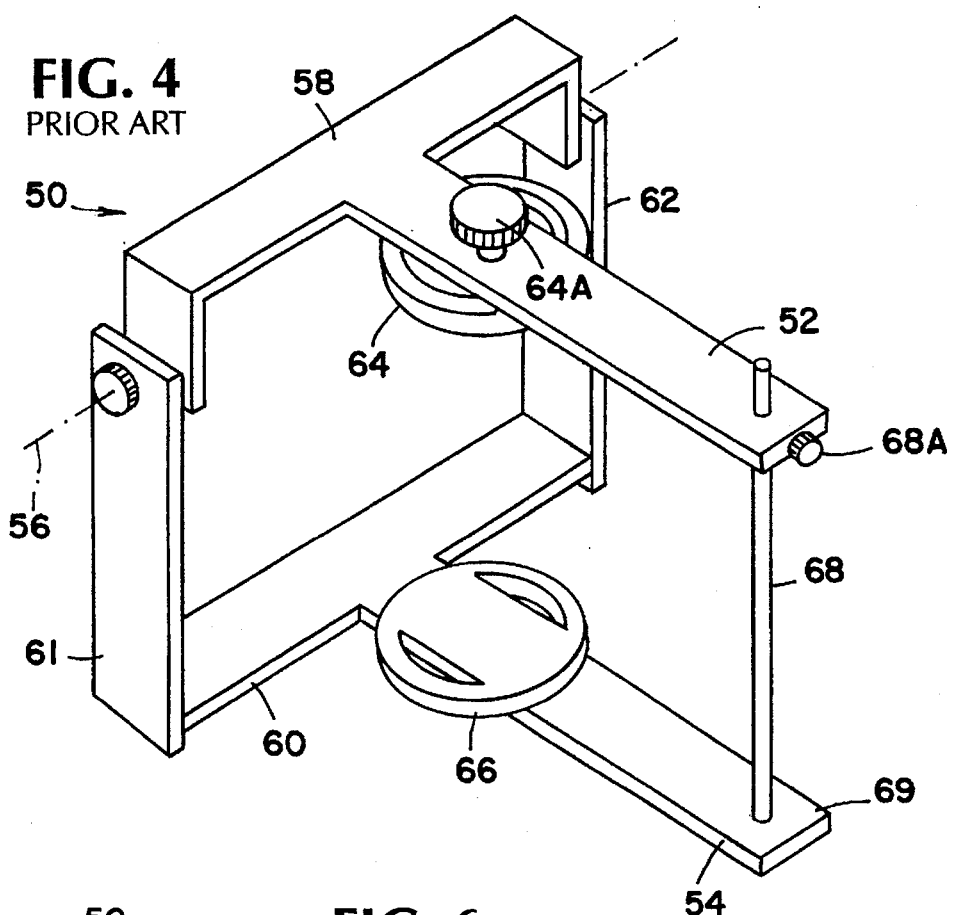
FIG. 4 is a perspective view of a prior art articulator shown in simplified form.

Articulator 50 of FIG. 4 has an upper arm 52 pivotally connected to a lower arm 54 so as to articulate about such lower arm along an axis 56. Upper arm 52 is supported by an upper beam 58; and lower arm 54 is supported by a lower beam 60 and upright columns 61 and 62. An upper, or maxillary, arch plate 64 depends downwardly from upper arm 52, and is held in position by a bolt 64A; and a corresponding lower, or mandibular, arch plate 66 depends upwardly from lower arm 54 and is held in place by a corresponding bolt (not shown). An incisal pin 68 is held to upper arm 52 with a bolt 68A. Incisal pin 68 rests on incisal plate 69, which may comprise part of the upper surface of lower arm 54.

In articulator 50, above-mentioned axis 56 is a simulated axis of rotation of the condyle of the lower jaw of a patient. In using the articulator, a model (not shown) of an upper, or maxillary, arch of a patient is first mounted to maxillary arch plate 64, with respect to the mentioned simulated axis of rotation 56. Then a model (not shown) of the lower, or mandibular, arch of the patient is mounted to mandibular arch plate 66.

FIG. 5 shows a novel cast (or model) relator device 75 that can be used in conjunction with the articulator of FIG. 4. The articulator is shown in phantom for ease of viewing its relationship to model relator 75. Relator 75 includes a base member 76 against which an upright support beam 78 is mounted. Attached to upright support beam 78 is a table 80 used for supporting a model of an upper, or maxillary, arch of a patient. Table 80 may be secured to upright beam 78 with a bolt 81, preferably having a knob 82 to facilitate its turning. The detail plan view of FIG. 5A, taken at arrow 84 in FIG. 5, shows how base member 76 of relator 75 (FIG. 5) cooperates with lower arm 54 and lower beam 60 of the articulator.

As shown in FIG. 5A, side 76A of base member 76 may abut lower arm 54 of the articulator. This positions table 80 (FIG. 5), as viewed left-to-right in FIG. 5, so that such table, and specifically, incisal pin 80A (FIG. 5), will be centrally located above mandibular arch plate 66 (e.g., FIG. 4). This approach requires that base member 76 be dimensioned for use with any particular articulator. Alternatively, base member 76 could incorporate a spacing mechanism (not shown) for left-to-right positioning of the base member with respect to lower arm 54 so as to achieve the desired positioning of table 80 (FIG. 5).

As further shown in FIG. 5A, base member 76 does incorporate a spacing mechanism 76B, 76C for spacing the base member top-to-bottom in FIG. 5A; this corresponds to spacing front-to-back with respect to models (not shown) of a patient's maxillary and mandibular arches. "Front-to-back" spacing or positioning is meant to signify throughout this specification and appended claims, spacing or positioning front-to-back on either a patient's head or models of a patient's maxillary or mandibular arches. Spacing mechanism 76B, 76C comprises a beam 76B that is slidable top-to-bottom in FIG. 5A within a slot 76C, shown more clearly in FIG. 5. The relatively enlarged lower part of beam 76B fits within a relatively enlarged lower part of slot 76C; this prevents beam 76B from being pulled straight up from slot 76C. A knob section 76D of a bolt that passes vertically through beam 76B can be turned to press against the bottom of slot 76C, whereby beam 76B is held in position relative to the remainder of base member 76. Preferably, beam 76B bears a scale 76E for convenient adjustment of spacing mechanism 76B, 76C, the importance of which adjustment will be mentioned below.

With reference to FIG. 5, the vertical position of table 80 can be adjusted by sliding the table up or down on upright beam 78, and then turning knob 82 to secure the table at a desired vertical position. The importance of such vertical adjustment will be mentioned below. Preferably, as shown in the detail view of FIG. 5B, taken at arrow 86 in FIG. 5 and showing upright beam 78 and table 80, upright beam 78 has a scale 78A to facilitate the desired positioning of table 80 relative to such upright beam.

As shown in FIG. 5, table 80 includes means 80A, 80C for supporting a model (not shown) of a maxillary arch of a patient. Means 80A may conveniently comprise an upwardly projecting incisal pin, which passes vertically through slot 80B in the table, and which, as shown in the detail view of FIG. 5C, is secured to table 80 with a bolt 80E received within pin 80A. Slot 80B is oriented to allow incisal pin 80A to be adjustable in a front-to-back position with respect to axis of rotation 56 of articulator 50.

Support means 80C may conveniently comprise a metal strip or blade contained in a notch 80D of the table, and used to support hamular notches of a maxillary model, as will be detailed below. Notch 80D is oriented substantially orthogonally to slot 80B, and also generally parallel to axis 56 of the articulator. Preferably, the height of incisal pin 80A is substantially the same as the height of hamular strip or blade 80C, for purposes explained below.

FIG. 6 illustrates the positioning of a model 100 of a maxillary arch of a patient with respect to a simulated axis 56 of rotation of the condyle of a patient's mandibular, or lower, jaw. Plaster mounting 102 between maxillary arch plate 64 and maxillary model 100 is shown in phantom. This is because such mounting 102 only constructed after maxillary model 100 has been properly positioned. In order to position table 80, referring to FIG. 5A, base member side 76A is brought into abutment with lower arm 54 of the articulator; alternatively, as mentioned above, a spacing mechanism (not shown) may be used to position base member 76 with respect to lower arm 54. Proper position is reached when incisal pin 80A (FIG. 6) is centrally located beneath upper arm 52 in a side-to-side direction in FIG. 6 (e.g., in a direction parallel to axis 56).

Front-to-back positioning of table 80 is achieved, referring to FIG. 5A, by adjusting beam 76B along its slot 76C so that it abuts lower beam 60, on the one hand. On the other hand, referring also to the radiographic image of FIG. 3, beam 76B is adjusted in its slot 76C so that the front-to-back distance 34 determined with respect to FIG. 3 is replicated between simulated axis of rotation 56 and hamular blade 80C. Hamular blade 80C is intended to support the hamular notches of maxillary model 100, and thus corresponds with pointer 20 in FIG. 3 positioned on a patient's hamular notch.

Referring back to FIG. 6, vertical positioning of table 80 is achieved by adjusting the vertical position of the table along upright beam 78. Proper vertical positioning of table 80 is reached when the vertical distance from the top of hamular blade 80C to simulated axis 56 of rotation replicates distance 36 shown in FIG. 3.

As mentioned above, distances 34 and 36 from FIG. 3 are, of course, adjusted for any scaling (e.g. reduction) of the radiographic image of FIG. 3.

Upon adjusting the foregoing, various distances, maxillary model 100 is then positioned atop support means 80A, 80C of table 80. Specifically, the hamular notches of model 100, corresponding to locations 14 and 16 in FIG. 1, are made to rest on hamular blade 80C. The front-to-back position of incisal pin 80A is then adjusted so that such pin supports the incisive papilla of the model, corresponding to point 12 in FIG. 1. As mentioned above, the top of incisal pin 80A and the top of hamular blade 80C are preferably in a substantially horizontal plane. As a result, maxillary model 100 becomes predictably and reliably positioned despite the fact that the bottom of a patient's upper teeth on the left side, for instance, may be substantially higher that the bottom of the patient's upper teeth on the right side. If a prior art face bow (described above) is used, rather than the present invention, the plane of the foregoing patient's hamular notches and incisive papilla will tilt to the patient's left side. Such tilting is undesirable because it perpetuates the misalignment, and hinders the doctor from viewing discrepancies in the dental arch.

FIG. 7 is a view similar to FIG. 6, additionally showing, however, a model 120 of a mandibular arch of a patient and its supporting plaster mounting 122 formed atop mandibular arch plate 66 of articulator 50. Additionally, cast relator device 75 (e.g., FIG. 6) is not shown in FIG. 7, since its purpose of aligning table 80 as described above has been fulfilled. Basically, once model 100 of the maxillary arch has been positioned upon plaster cast 102, model 120 of a mandibular arch is then positioned beneath model 100.

Preferably, model 120 is positioned beneath model 100 in the same relative position to upper model 100 as was the case when the patient poses for the, e.g., radiographic image of FIG. 3. For instance, if the image of FIG. 3 were taken with the patient's teeth in a closed-bite position, lower model 120 should be positioned beneath upper model 120 in the same closed-bite position. If the upper teeth are separated from the lower teeth by a spacer, then lower model 120 should likewise be separated from upper model 100 by a spacer of the same dimension.

While the invention has been described with respect to specific embodiments by way of illustration, many modifications and changes will occur to those skilled in the art. For instance, while it is preferred that an image like that of FIG. 3 be taken while the patient's hamular notches and incisive papilla lie in a substantially horizontal plane, such image can alternatively be taken while such landmarks are in a plane with a different orientation. In such case, of course, the different orientation would be taken into account in determining the vertical and front-to-back positioning of the condyle axis and hamular notch as described above with respect to FIG. 3. It is, therefore, to be understood that the appended claims are intended to cover all such modifications and changes as fall within the true scope and spirit of the invention.

What is claimed is:

1. A method of relating a model of a maxillary arch of a patient to a simulated axis of rotation of the condyle of the lower jaw of the patient, comprising the steps of:

(a) positioning a pointer on a predetermined landmark of the upper jaw of a patient;

(b) obtaining a lateral image of said condyle and said pointer while the patient's two hamular notches and incisive papilla define a plane that is substantially horizontal;

(c) determining from said image vertical and front-to-back distances of the axis of rotation of said condyle relative to said landmark;

(d) positioning a model of a maxillary arch of a patient such that said predetermined landmark is located with substantially the same vertical and front-to-back distances from a simulated axis of rotation of the patient's lower jaw; and (e) positioning a model of the patient's lower jaw that rotates about said simulated axis so as to abut said model of the maxillary arch.

2. The method of claim 1, wherein said step of obtaining a lateral image comprises obtaining said image when said lower jaw is abutting said upper jaw in a closed-bite position.

3. The method of claim 1, wherein said predetermined landmark comprises a hamular notch.

4. The method of claim 1, wherein said step of positioning a model of a maxillary arch comprises additionally positioning the foregoing model such that said already-mentioned landmark and two additional landmarks of said upper jaw lie in a substantially horizontal plane.

5. The method of claim 4, wherein said already-mentioned landmark comprises a hamular notch, and said two additional landmarks comprise a further hamular notch and an incisive papilla.

6. A method of relating a model of a maxillary arch of a patient to a simulated axis of rotation of the condyle of the lower jaw of the patient, comprising the steps of:

(a) positioning a pointer on a predetermined landmark of the upper jaw of a patient;

(b) obtaining a lateral image of said condyle and said pointer while the patient's two hamular notches and incisive papilla define a predetermined plane;

(c) determining from said image vertical and front-to-back distances of the axis of rotation of said condyle relative to said landmark;

(d) positioning a model of a maxillary arch of a patient such that said predetermined landmark is located with substantially the same vertical and front-to-back distances from a simulated axis of rotation of the patient's lower jaw; and (e) positioning a model of the patient's lower jaw that rotates about said simulated axis so as to abut said model of the maxillary arch.

7. The method of claim 6, wherein said step of obtaining a lateral image comprises obtaining said image when said lower jaw is abutting said upper jaw in a closed-bite position.

8. The method of claim 6, wherein said predetermined landmark comprises a hamular notch.

9. In combination with an articulation device for mounting a model of a maxillary arch of a patient to one side of a hinge of the articulation device, and mounting a model of a mandibular arch of the patient to the other side of said hinge, a device for relating the position of a maxillary model of a patient to an axis of rotation of said hinge of said articulator, comprising:

(a) means for supporting said maxillary model in an initially unattached relation to said articulation device, said means including three points of support for the model of the patient's maxillary arch, said three points defining a plane substantially parallel to a true horizontal plane; and (b) means for adjustably positioning said maxillary model at any point along a substantial range of vertical and front-to-back positions relative to said axis of rotation.

10. The combination of claim 9, wherein said means for positioning includes a support table for said maxillary model and a vertical beam adjustably supporting said table at any point along a substantial range of heights along said vertical beam without tilting said table as between different heights.

11. The combination of claim 10, further comprising a scale associated with said vertical beam for measuring the vertical height of said table.

12. The combination of claim 9, wherein said means for positioning includes a support table for said maxillary model and a spacing mechanism for adjustably spacing said table at any point along a substantial range of front-to-back positions relative to said axis of rotation.

13. The combination of claim 11, wherein said means for supporting said maxillary model includes a table with an incisal pin for supporting an incisive papilla of said maxillary model.

14. The combination of claim 13, wherein said means for supporting said maxillary model further includes means for supporting a pair of hamular notches of said maxillary model.

15. The combination of claim 12, further comprising a scale associated with said spacing mechanism for measuring the front-to-back spacing of said table relative to said axis of rotation.

* * * * *